(12) United States Patent
Pazenok et al.

(10) Patent No.: US 8,436,191 B2
(45) Date of Patent: May 7, 2013

(54) PREPARING 5-FLUORO-1-ALKYL-3-FLUOROALKYL-1H-PYRAZOLE-4-CARBONYL CHLORIDES

(75) Inventors: Sergii Pazenok, Solingen (DE); Norbert Lui, Odenthal (DE); Marc Kosten, Weyhe (DE); Guenter Bartels, Burgwedel (DE)

(73) Assignee: Bayer CropScience AG (DE)

( * ) Notice: Subject to any disclaimer, the term of this patent is extended or adjusted under 35 U.S.C. 154(b) by 101 days.

(21) Appl. No.: 12/950,849

(22) Filed: Nov. 19, 2010

(65) Prior Publication Data

US 2011/0207940 A1    Aug. 25, 2011

Related U.S. Application Data

(60) Provisional application No. 61/262,641, filed on Nov. 19, 2009.

(30) Foreign Application Priority Data

Nov. 19, 2009   (EP) ...................................... 09176426

(51) Int. Cl.
    *C07D 231/20*    (2006.01)
(52) U.S. Cl.
    USPC ..................................... 548/366.1; 548/374.1

(58) Field of Classification Search ........................ None
    See application file for complete search history.

(56) References Cited

U.S. PATENT DOCUMENTS

| 5,675,016 | A | 10/1997 | Gallenkamp et al. |
| 7,714,144 | B2 * | 5/2010 | Neeff et al. ................ 548/374.1 |
| 2009/0306401 | A1 | 12/2009 | Neeff et al. |
| 2010/0041899 | A1 | 2/2010 | Lui et al. |

FOREIGN PATENT DOCUMENTS

| EP | 1 364 946 A1 | 11/2003 |
| WO | WO 2006/018725 A1 | 2/2006 |
| WO | WO 2007/087906 A1 | 8/2007 |

OTHER PUBLICATIONS

Lee, L.F., et al., "Synthesis and $^{13}C$ NMR of (Trifluoromethyl)hydroxypyrazoles," *J.Heterocyclic Chem.* 27:243-245, Journal of Heterocyclic Chemistry, United States (1990).

* cited by examiner

*Primary Examiner* — Kamal Saeed
(74) *Attorney, Agent, or Firm* — Sterne, Kessler, Goldstein & Fox P.L.L.C.

(57) ABSTRACT

The present invention relates to a novel process for preparing 5-fluoro-1-alkyl-3-fluoroalkyl-1H-pyrazole-4-carbonyl chlorides, a useful intermediate in the manufacture of fungicides.

5 Claims, No Drawings

PREPARING 5-FLUORO-1-ALKYL-3-FLUOROALKYL-1H-PYRAZOLE-4-CARBONYL CHLORIDES

The present application claims priority to U.S. Provisional Patent Application No. 61/262,641, filed Nov. 19, 2009, which is hereby incorporated by reference in its entirety.

The present invention relates to a novel process for preparing 5-fluoro-1-alkyl-3-fluoroalkyl-1H-pyrazole-4-carbonyl chlorides, a useful intermediate in the manufacture of fungicides.

Pyrazolecarbonyl chlorides are important synthons for preparing crop protection actives. Pyrazolecarbonyl chlorides are typically prepared by reacting carboxylic acids with a chlorinating agent. One advantage of this method is that appropriate carboxylic acids are easy to obtain and hence available on an industrial scale. This prerequisite is not satisfied in the case of the preparation of substituted pyrazolecarbonyl chlorides, since the corresponding carboxylic acids are not readily available.

It has now been found that 5-fluoro-1-alkyl-3-fluoroalkyl-1H-pyrazole-4-carbonyl chlorides of formula (I)

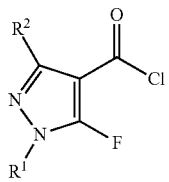

(I)

where $R^1$ represents $C_1$-$C_6$-alkyl and $R^2$ represents $C_1$-$C_5$-fluoroalkyl, are obtained when 5-chloro-1-alkyl-3-fluoroalkyl-1H-pyrazole-4-carbaldehyde of formula (II)

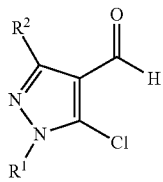

(II)

where $R^1$ and $R^2$ are each as defined above,
is initially reacted (step 1) with a fluorinating agent of formula (III)

$$M^+F^-$$ (III)

where $M^+$ represents $Li^+$, $Na^+$, $K^+$, $Cs^+$, $Alk_4N^+$ (where Alk represents $C_1$-$C_4$-alkyl),
and optionally in the presence of a phase transfer catalyst to form 5-fluoro-1-alkyl-3-fluoroalkyl-1H-pyrazole-4-carbaldehyde of formula (IV)

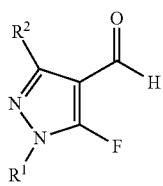

(IV)

where $R^1$ and $R^2$ are each as defined above, and then the compounds of formula (IV) are converted by reaction with a chlorinating agent (step 2) into the acyl chlorides of formula (I).

The process according to the invention can be illustrated by the following formula scheme:

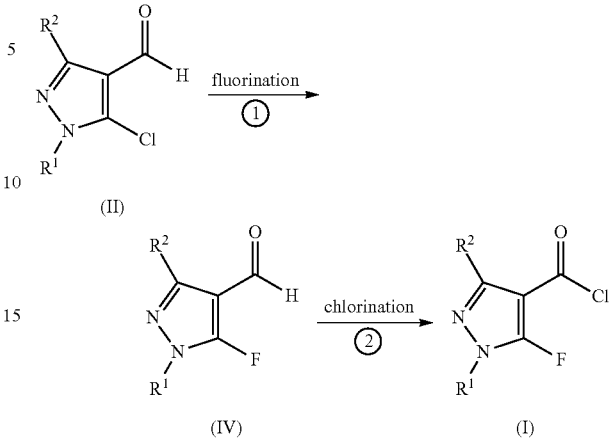

The 5-chloro-1-alkyl-3-fluoroalkyl-1H-pyrazole-4-carbaldehydes used as starting materials in the process according to the invention are defined generically by the formula (II). The radical $R^1$ in this formula (II) preferably represents methyl, ethyl, n-propyl, isopropyl, butyl, pentyl, and more preferably represents methyl. The radical $R^2$ represents $C_1$-$C_5$-fluoroalkyl, wherein fluoroalkyl is an alkyl group having 1 to 5 carbon atoms which is substituted with at least one fluorine atom up to the point of perfluorination. When the fluoroalkyl is not perfluorinated, further halogen atoms such as chlorine and bromine, preferably chlorine, can be present as further substituents. $R^2$ preferably represents $CF_2H$, $CF_3$, $CF_2Cl$, $CCl_2F$, $C_2F_5$, $C_3F_7$, and more preferably represents $CF_2H$ and $CF_3$. Very particular preference is given to using 5-chloro-1-methyl-3-difluoromethyl-1H-pyrazole-4-carbaldehyde (II-1) as starting material.

5-Chloro-1-alkyl-3-fluoroalkyl-1H-pyrazole-4-carbaldehydes of formula (II) are known or obtainable by known methods (cf. *J. Het. Chem.* 1990, 27, 243, WO 2006/018725).

5-Chloro-1-alkyl-3-fluoroalkyl-1H-pyrazole-4-carbaldehydes of formula (II) are obtainable for example by
(a) reacting esters of formula (VI)

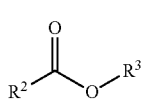

(VI)

where $R^2$ is as defined above and $R^3$ represents methyl or ethyl,
with ethyl acetate in the presence of a base (sodium hydride for example) and in the presence of a diluent (tetrahydrofuran for example) to form β-ketoesters of formula (VII)

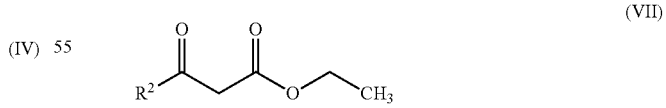

(VII)

where $R^2$ is as defined above, and reacting these
(b) with alkylhydrazines of formula (VIII)

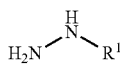

(VIII)

where $R^1$ is as defined above, in the presence of a diluent (toluene for example) to form 5-hydroxy pyrazoles of formula (IX)

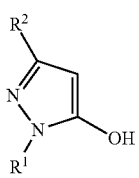
(IX)

where $R^1$ and $R^2$ are each as defined above, and reacting these (c) in a last step with a chlorinating agent (phosphoryl chloride for example) in the presence of a diluent (toluene for example) and in the presence of dimethylformamide.

The fluorides needed in addition as a starting material, for example sodium fluoride and potassium fluoride, are known synthesis chemicals.

Step 1: Fluorination

Processes for exchanging chlorine for fluorine (halex processes) are known particularly for 5-chloro-1,3-dialkyl-1H-pyrazole-4-carbonyl chlorides (cf. for example WO 2007/031212 and EP-A 0 776 889). The acyl chloride is converted into the acyl fluoride and as a result the fluorination is speeded in addition. If, however, the activation group is the aldehyde CHO instead of the acyl chloride COCl or instead of the acyl fluoride COF, the reaction with potassium fluoride provides very low yields only. For example, 5-fluoro-1,3-dimethyl-1H-pyrazole-4-carbaldehyde is obtained by reaction of 1,3-dimethyl-5-chloropyrazole-4-carbaldehyde with potassium fluoride in a 24% yield only (EP-A 0 776 889). One possible reason for the poor yield is the low thermal stability of pyrazolealdehydes (cf. EP-A 1 364 946). It is unforeseeable whether the fluorination of 5-chloro-1-alkyl-3-fluoroalkyl-1H-pyrazole-4-carbaldehydes with metal fluorides might be successful.

Surprisingly, the fluorination of 5-chloro-1-alkyl-3-fluoroalkyl-1H-pyrazole-4-carbaldehydes with metal fluorides leads selectively and in high yield to the novel 5-fluoro-1-alkyl-3-fluoroalkyl-1H-pyrazole-4-carbaldehyde.

Reaction temperatures in the process according to the invention can vary within wide limits. Temperatures are generally in the range from 120° C. to 200° C., preferably in the range from 110° C. to 180° C.

Reaction time can be up to 20 hours depending on the reactivity of the starting materials, although the reaction can also be terminated earlier when conversion is complete. Preference is given to reaction times of 3-10 hours.

The process according to the invention is carried out by using generally between 0.8 and 1.8 mol and preferably between 1 and 1.5 mol of fluorinating agent of formula (III) per mole of 5-chloro-1-alkyl-3-fluoroalkyl-1H-pyrazole-4-carbaldehyde of formula (II).

The reaction can be carried out with or without a solvent. Suitable solvents are sulpholane, dimethyl sulphoxide (DMSO), dimethylacetamide, dimethylformamide (DMF), N-methylpyrrolidone (NMP), 1,3-dimethylimidazolinone, dichloroethane, chloroform, dichloroethane, nitriles, such as acetonitrile, propionitrile, n- or i-butyronitrile or hexamethylphosphoramide. Particular preference is given to using sulpholane, DMSO, dimethylacetamide, DMF or NMP.

The fluorination can be speeded by adding phase transfer catalysts.

The quaternary ammonium compounds, phosphonium compounds or amidophosphonium salts useful as phase transfer catalysts in the process according to the invention include tetrabutylphosphonium chloride, tetrabutylphosphonium bromide, tetraphenylphosphonium chloride or tetraphenylphosphonium bromide, tetrakis(dimethylamino)phosphonium chloride or bromide, tetrakis(diethylamino) phosphonium chloride or bromide, tetrakis(dipropylamino) phosphonium chloride or bromide, tris(diethylamino) (dimethylamino)-phosphonium chloride or bromide, tris (dimethylamino)(cyclohexylamino)phosphonium chloride or bromide, tris(dimethylamino)(diallylamino)phosphonium chloride or bromide, tris(dimethylamino)-(dihexylamino) phosphonium chloride or bromide, tris(diethylamino)(dihexylamino)phosphonium chloride or bromide, tris(pyrrolidino)(ethylmethylamino)phosphonium chloride or bromide, tris(pyrrolidino)-(diethylamino)phosphonium chloride or bromide, hexaalkylguanidinium salts or polyethylene glycol dimethyl ethers of chain length r from 6 to 17 and average molar mass of 500 g/mol.

Step 2: Chlorination

Some of the 5-fluoro-1-alkyl-3-fluoroalkyl-1H-pyrazole-4-carbaldehydes of formula (IV) needed as starting materials are novel (for example 5-fluoro-1-alkyl-3-trifluoromethyl-1H-pyrazole-4-carbaldehyde is described in WO-A 2004/014138).

$R^1$ in this formula (IV) preferably represents methyl, ethyl, n-propyl, isopropyl, butyl, pentyl, and more preferably represents methyl. The radical $R^2$ represents $C_1$-$C_5$-fluoroalkyl, wherein fluoroalkyl is an alkyl group having 1 to 5 carbon atoms which is substituted with at least one fluorine atom up to the point of perfluorination. When the fluoroalkyl is not perfluorinated, further halogen atoms such as chlorine and bromine, preferably chlorine, can be present as further substituents. $R^2$ preferably represents $CF_2H$, $CF_3$, $CF_2Cl$, $CCl_2F$, $C_2F_5$, $C_3F_7$, and more preferably represents $CF_2H$ and $CF_3$. Very particular preference is given to 5-fluoro-1-methyl-3-difluoromethyl-1H-pyrazole-4-carbaldehyde (IV-1) and 5-fluoro-1-methyl-3-trifluoromethyl-1H-pyrazole-4-carbaldehyde (IV-2), more particularly the compound (IV-1).

The chlorination of pyrazolealdehydes to the acyl chloride was described in WO-A 2008/086962.

It is customary to use the 5-fluoro-1-alkyl-3-fluoroalkyl-1H-pyrazole-4-carbaldehyde of formula (IV) and the chlorinating agent in a molar ratio ranging from 1:3 to 1:2, and preferably ranging from 1:1.4 to 1:1.

The chlorinating agent used can be chlorine or a chlorine-releasing reagent. The reaction can optionally be carried out in the presence of an inert diluent gas such as, for example, nitrogen, carbon dioxide or noble gases. Suitable chlorinating agents, without making any claim to completeness, are for example $Cl_2$, $SO_2Cl_2$, $SOCl_2$, N-chlorosuccinimide or a mixture thereof. Preference is given to using $Cl_2$, $SO_2Cl_2$ or a mixture thereof as chlorinating agent. Particular preference is given to $SO_2Cl_2$ and $Cl_2$ as chlorinating agent.

The reaction of 5-fluoro-1-alkyl-3-fluoroalkyl-1H-pyrazole-4-carbaldehydes of formula (IV) with the chlorinating agent is customarily carried out in the presence of a diluent which behaves inertly under the prevailing reaction conditions. Useful diluents include for example mono- or polychlorinated aliphatic or aromatic hydrocarbons or mixtures thereof. Examples of suitable diluents are chlorobenzene, dichlorobenzenes, trichlorobenzenes, chlorotoluenes, chlorobenzotrifluorides, methylene chloride, dichloroethane, chloroform, carbon tetrachloride. Preferred diluents are chlorobenzene, 1,2-dichlorobenzene, 1,3-dichlorobenzene, 1,4-dichlorobenzene, 1,2,3-trichlorobenzene, 1,2,4-trichlorobenzene, 4-chlorotrifluoromethylbenzene, 1,3,5-trichlorobenzene, 2-chlorotoluene, 3-chlorotoluene, 4-chlorotoluene or a mixture thereof. Particular preference is given to using chlorobenzene and dichlorobenzene.

According to the present invention, the chlorination is effected under free-radical conditions. The prerequisite for this is the formation of free chlorine radicals.

It is known that organic peroxides or azo compounds will decompose under the action of heat and/or light into free radicals which initiate the free-radical chlorination.

Examples, without claim to completeness, of suitable peroxides and azo compounds are tert-butylhydro peroxide, dibenzoyl peroxide, di(4-tert-butylcyclohexyl) peroxydicarbonate, 2,2'-azobis(isobutyronitrile), dimethyl 2,2'-azobis(isobutyrate), 2,2'-azobis(2,4-dimethylvaleronitrile), di(2-ethylhexyl) peroxy-dicarbonate, tert-butyl peroxypivalate, tert-amyl peroxy-2-ethylhexanoate, tert-butyl peroxy-2-ethylhexanoate.

Preference is given to using the following free-radical initiators: 2,2'-azobis(isobutyronitrile), 2,2'-azobis(2,4-dimethylvaleronitrile), di(2-ethylhexyl) peroxydicarbonate, tert-amyl peroxy-2-ethylhexanoate, tert-butyl peroxy-2-ethylhexanoate. The free-radical initiator is typically used in an amount of 0.01 to 1 mol % and preferably 0.1 to 0.5 mol % based on the aldehyde of formula (IV).

All processes according to the invention are generally carried out under atmospheric pressure. However, it is also possible to use elevated or reduced pressure—generally between 0.1 bar and 10 bar.

Instead of the chlorination, the 5-fluoro-1-alkyl-3-fluoroalkyl-1H-pyrazole-4-carbaldehydes of formula (IV) can alternatively be converted by reaction with a perhaloacid (periodic acid for example) in the presence of a diluent (acetonitrile for example) and in the presence of an oxidizing agent (PCC for example) into the 5-fluoro-1-alkyl-3-fluoroalkyl-1H-pyrazole-4-carboxylic acids of formula (V)

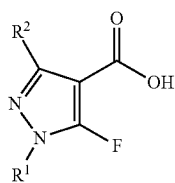

(V)

where $R^1$ and $R^2$ are each as defined above.

Not only the 5-fluoro-1-alkyl-3-fluoroalkyl-1H-pyrazole-4-carbaldehydes of formula (IV) but also the 5-fluoro-1-alkyl-3-fluoroalkyl-1H-pyrazole-4-carboxylic acids of formula (V) are important intermediates in the synthesis of crop protection agents (cf. for example European Patent Application No. 09356038.7 and WO-A 2007/087906).

Preparing 5-fluoro-1,3-dialkyl-1H-pyrazole-4-carbonyl chlorides of formula (I) in a manner according to the invention is described in the examples which follow, which further illustrate the above description. However, the examples shall be interpreted in a nonlimiting manner.

PREPARATION EXAMPLES

Example 1

5-fluoro-1-methyl-3-difluoromethyl-1H-pyrazole-4-carbaldehyde (IV-1)

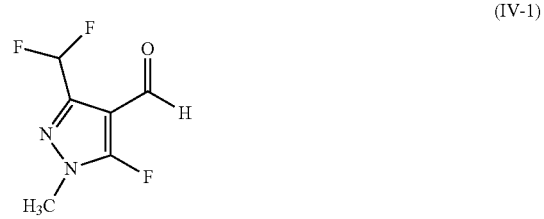

(IV-1)

Under argon 19.4 g (100 mmol) of 5-chloro-1-methyl-3-difluoromethyl-1H-pyrazole-4-carbaldehyde (II-1) were initially charged in dimethylformamide. This was followed by the addition of 8.6 g (150 mmol) of potassium fluoride (KF water content 0.05%), heating to 150° C. and subsequent stirring at that temperature for 8 hours. This was followed by dilution of the mixture with ethyl acetate, filtration and distillative removal of the solvent in vacuo at 0.5 mbar and 70° C. to obtain 16 g (90% of theory) of 5-fluoro-1-methyl-3-difluoromethyl-1H-pyrazole-4-carbaldehyde having a purity of 99% (melting point 68° C.).

$^1$H NMR (CD$_3$CN): δ=9.8 (1H, s), 6.88 (1H, t), 3.7 (3H, s) ppm.

$^{19}$F NMR (CD$_3$CN): δ=−114.75 (2F, t), −124.06 (1F, s) ppm.

Example 2

5-fluoro-1-methyl-3-difluoromethyl-1H-pyrazole-4-carbaldehyde (IV-1)

96.3 g (1660 mmol) of spray-dried potassium fluoride were carefully dried under high vacuum. 129.2 g (664 mmol) of 5-chloro-1-methyl-3-difluoromethyl-1H-pyrazole-4-carbaldehyde (II-1) in 1 L of DMF were added. The reaction mixture was heated to 150° C. with rapid stirring. The reaction is complete after 3 hours (GC check). The reaction mixture is cooled down to room temperature and bulked with water to a total volume of 4 L. The reaction mixture is washed twice with 2000 ml of ethyl acetate each time. The combined organic phases were subsequently washed with saturated sodium chloride solution, dried over sodium sulphate and concentrated to obtain 117.6 g (90% of theory, purity 90%) of 5-fluoro-1-methyl-3-difluoromethyl-1H-pyrazole-4-carbaldehyde (IV-1) in the form of a brown solid which is further reacted without further purification.

Example 3

5-fluoro-1-methyl-3-difluoromethyl-1H-pyrazole-4-carbonyl chloride (I-1)

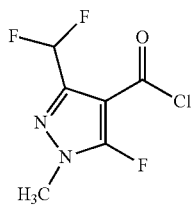

(I-1)

The solution of 17.8 g (100 mmol) of 5-fluoro-1-methyl-3-difluoromethyl-1H-pyrazole-4-carbaldehyde, 17.5 g (130 mmol) of sulphuryl chloride and 0.2 g of 2,2-azoisobutyronitrile in 50 ml of chlorobenzene was stirred at 80° C. for 6 hours.

The reaction solution was concentrated to obtain 20.1 g of the product as an oil having a purity (GC) of 98%.

$^1$H NMR (CD$_3$CN): δ=6.88 (1H, t), 3.7 (3H, s) ppm.

Example 4

3-(difluoromethyl)-5-fluoro-1-methyl-1H-pyrazole-4-carboxylic acid (V-1)

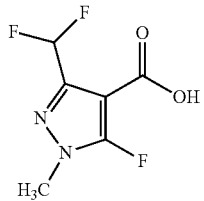

(V-1)

A suspension of 79.7 g (350 mmol) of periodic acid in 640 ml of absolute acetonitrile was stirred for 30 min. At 0° C., 56.6 g (318 mmol) of 5-fluoro-1-methyl-3-difluoromethyl-1H-pyrazole-4-carbaldehyde (IV-1) and 1.4 g (6 mmol) of PCC dissolved in 130 ml of dry acetonitrile were added. The reaction mixture was subsequently stirred at room temperature for 2.5 hours. After 1600 ml of ethyl acetate had been added, the reaction mixture was washed in succession with saturated sodium chloride solution/water (1:1), saturated sodium metabisulphite solution and saturated sodium chloride solution. The organic phase was dried over sodium sulphate and concentrated to obtain 51.4 g (83% of theory) of 3-(difluoromethyl)-5-fluoro-1-methyl-1H-pyrazole-4-carboxylic acid (V-1) as a yellow solid.

Example 5 ethyl 4,4-difluoro-3-oxobutanoate (VII-1)

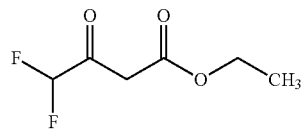

(VII-1)

Under nitrogen, 46.7 g (1.168 mol) of sodium hydride (60% dispersion in paraffin) were added to 600 ml of tetrahydrofuran. At 35° C. a mixture of 125 g (1.008 mol) of difluoroethyl acetate and 88.7 g (1.010 mol) of ethyl acetate was added dropwise while the temperature was maintained at below 40° C. This was followed by further stirring at room temperature overnight. The reaction mixture was carefully poured into 1.7 L of ice-water and adjusted to pH 3 with sulphuric acid. The reaction mixture was extracted twice with 500 ml of methyl tert-butyl ether each time, the combined organic phases were washed twice with saturated sodium chloride solution, dried over sodium sulphate and concentrated at 40° C. and 150 mbar before distillation at 60 mbar (Vigreux column). The product was obtained at 85-87° C. as a colourless liquid (104 g, 62% of theory having a purity of >99% (GC)).

Example 6

3-(difluoromethyl)-1-methyl-1H-pyrazol-5-ol (IX-1)

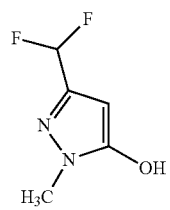

(IX-1)

To a solution of 208.6 g (1257 mmol) of ethyl 4,4-difluoro-3-oxobutanoate (VII-1) in 1000 ml of toluene was added 57.8 g (1257 mmol) of methylhydrazine by dropwise addition with cooling. After 90 min under reflux the reaction mixture was cooled down and concentrated. After 1500 ml of diethyl ether had been added, the reaction mixture was stirred and the insoluble material was filtered off. The filtrate was concentrated to obtain 137.5 g (74% of theory) of 3-(difluoromethyl)-1-methyl-1H-pyrazol-5-ol (IX-1) as a reddish orange solid which was used in the next reaction step without further purification.

Example 7

5-chloro-3-(difluoromethyl)-1-methyl-1H-pyrazole-4-carbaldehyde (II-1)

(II-1)

To a solution of 137.5 g (929 mmol) of 3-(difluoromethyl)-1-methyl-1H-pyrazol-5-ol (IX-1) in 136 ml (1858 mmol) of absolute dimethylformamide and 750 ml of toluene was added 571 g (3716 mmol) of phosphoryl chloride by dropwise addition with cooling. The reaction mixture was refluxed for 3 hours, cooled down and carefully poured into 4 L of ice-water. After extracting three times with 1500 mL of ethyl acetate each time, the combined organic phases were washed twice with saturated sodium bicarbonate solution and finally with saturated sodium chloride solution, dried over sodium sulphate and concentrated to obtain 129.2 g (72% of theory having a purity of >99% (GC)) of 5-chloro-3-(difluoromethyl)-1-methyl-1H-pyrazole-4-carbaldehyde (II-1) in the form of a reddish brown solid which was used in the next reaction step without further purification.

The invention claimed is:

1. A process for preparing a compound of formula (I)

(I)

where $R^1$ represents $C_1$-$C_6$-alkyl and $R^2$ represents $C_1$-$C_5$-fluoroalkyl that is optionally bromo- or chloro- substituted, wherein said process comprises reacting a compound of formula (II)

(II)

where $R^1$ and $R^2$ are as defined above,
with a fluorinating agent of formula (III)

$$M^+F^-$$ (III)

where $M^+$ represents $Li^+$, $Na^+$, $K^+$, $Cs^+$, $Alk_4N^+$ and Alk represents $C_1$-$C_4$-alkyl, and optionally in the presence of a phase transfer catalyst to give a compound of formula (IV)

(IV)

where $R^1$ and $R^2$ are as defined above, and further reacting a compound of formula (IV) with a chlorinating agent to give a compound of formula (I).

2. The process according to claim 1, wherein $R^1$ represents methyl, ethyl, n-propyl, isopropyl, butyl, pentyl and $R^2$ represents $CF_2H$, $CF_3$, $CF_2Cl$, $CCl_2F$, $C_2F_5$, or $C_3F_7$.

3. The process according to claim 1, wherein $R^1$ represents methyl and $R^2$ represents $CF_2H$ or $CF_3$.

4. The process according to claim 1, wherein the compound of formula II is 5-chloro-1-methyl-3-difluoromethyl-1H-pyrazole-4-carbaldehyde.

5. The process according to claim 1, wherein the compound of formula (II) is reacted with the compound of formula (III) in the presence of a phase transfer catalyst.

* * * * *